US006873875B1

(12) United States Patent
Gilkerson et al.

(10) Patent No.: US 6,873,875 B1
(45) Date of Patent: Mar. 29, 2005

(54) IMPLANTABLE PULSE GENERATOR AND METHOD HAVING ADJUSTABLE SIGNAL BLANKING

(75) Inventors: James O. Gilkerson, Stillwater, MN (US); Doug M. Birkholz, Shoreview, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/650,913

(22) Filed: Aug. 29, 2000

Related U.S. Application Data

(63) Continuation-in-part of application No. 09/377,803, filed on Aug. 20, 1999, now Pat. No. 6,304,778.

(51) Int. Cl.$^7$ .................................................. A61N 1/36
(52) U.S. Cl. ............................................ 607/9; 607/27
(58) Field of Search ...................... 607/9, 27; 128/901

(56) References Cited

U.S. PATENT DOCUMENTS

| | | | |
|---|---|---|---|
| 3,927,663 A | * 12/1975 | Russell et al. .............. | 600/515 |
| 4,386,610 A | 6/1983 | Leckrone .............. | 128/419 PG |
| 4,432,362 A | 2/1984 | Leckrone et al. ..... | 128/419 PG |
| 4,527,567 A | 7/1985 | Fischler et al. ........ | 128/419 PT |
| 4,550,370 A | 10/1985 | Baker ......................... | 364/413 |
| 4,558,702 A | 12/1985 | Barreras et al. ............ | 128/419 |
| 4,674,508 A | 6/1987 | DeCote ...................... | 128/419 |
| 4,674,509 A | 6/1987 | DeCote, Jr. ................. | 128/419 |
| 4,677,986 A | 7/1987 | DeCote, Jr. ................. | 128/697 |
| 4,721,114 A | 1/1988 | DuFault et al. ............. | 128/696 |
| 4,779,617 A | 10/1988 | Whigham ................ | 128/419 P |
| 4,819,643 A | 4/1989 | Menken .................. | 128/419 P |
| 4,825,869 A | 5/1989 | Sasmor et al. ......... | 128/419 PT |
| 4,928,674 A | 5/1990 | Halperin et al. ........... | 128/30.2 |
| 4,974,589 A | * 12/1990 | Sholder .......................... | 607/9 |

(Continued)

FOREIGN PATENT DOCUMENTS

EP 0707866 9/1995 .......... A61N/1/365

OTHER PUBLICATIONS

Gilkerson, James O., et al., "Implantable Defibrillators with Programmable Cross–Chamber Blanking", U.S. Appl. No. 10/756,897, filed Jan. 14, 2004 Attorney Docket No. 279.214US3, 16 Pgs.

Guidant Corporation, "Guident Announces First Six Implants of Ventak Prizm Defibrillation System ", *Guident New Release, www.guidant.com,* (Dec. 2, 1999), 1 Pg.

*Primary Examiner*—Angela D. Sykes
*Assistant Examiner*—Roderick Bradford
(74) *Attorney, Agent, or Firm*—Schwegman, Lundberg, Woessner & Kluth, P.A.

(57) ABSTRACT

An implantable pulse generator and a method of operation, where the pulse generator is adapted to sense at least a first cardiac signal. Cardiac events are identified in the first cardiac signal, in response to which a blanking interval is started. The blanking interval includes a repeatable noise window blanking interval. When noise is detected during the repeatable noise window blanking interval, the noise window blanking interval is repeated. Depending upon the type of sensed cardiac event (paced or intrinsic) the blanking interval is adjusted to either to a first overall duration or a second overall duration. The second overall duration includes a first timed interval that has a programmable value. The repeatable noise window blanking interval starts after the first timed interval of the second overall duration. The duration of repeated repeatable noise window blanking intervals is summed and compared to a pacing escape interval. When the sum is greater than the pacing escape interval, asynchronous pacing pulses are delivered. When the noise ceases, so does the delivery of asynchronous pacing pulses. Alternatively, when the sum is greater than the pacing escape interval, the pace escape interval is repeated. Pacing is resumed after one pacing escape interval after the noise signal ceases.

33 Claims, 10 Drawing Sheets

U.S. PATENT DOCUMENTS

| | | | |
|---|---|---|---|
| 5,010,888 A | 4/1991 | Jadvar et al. | 128/696 |
| 5,107,833 A | 4/1992 | Barsness | 128/419 T |
| 5,127,401 A | 7/1992 | Grevious et al. | 128/419 |
| 5,184,615 A | 2/1993 | Nappholz et al. | 128/419 P |
| 5,231,987 A | 8/1993 | Robson | 607/29 |
| 5,233,983 A | 8/1993 | Markowitz | 607/42 |
| 5,233,986 A | 8/1993 | Robson | 607/4 |
| 5,243,976 A | 9/1993 | Ferek-Petric et al. | 607/6 |
| 5,251,622 A | 10/1993 | Robson | 607/19 |
| 5,265,603 A | 11/1993 | Hudrlik | 607/9 |
| 5,265,617 A | 11/1993 | Verrier et al. | 128/704 |
| 5,289,824 A | 3/1994 | Mills et al. | 128/696 |
| 5,300,093 A | 4/1994 | Koestner et al. | 607/32 |
| 5,311,183 A | 5/1994 | Mathews et al. | 342/26 |
| 5,316,001 A | 5/1994 | Ferek-Petric et al. | 128/661.08 |
| 5,317,269 A | 5/1994 | Mills et al. | 324/427 |
| 5,321,445 A | 6/1994 | Fossetti | 607/9 |
| 5,333,616 A | 8/1994 | Mills et al. | 128/696 |
| 5,336,244 A | 8/1994 | Weijand | 607/21 |
| 5,342,406 A | 8/1994 | Thompson | 607/22 |
| 5,351,695 A | 10/1994 | Mills et al. | 128/696 |
| 5,366,488 A | 11/1994 | Franberg et al. | 607/9 |
| 5,372,135 A | 12/1994 | Mendelson et al. | 128/633 |
| 5,379,775 A | 1/1995 | Kruse | 128/697 |
| 5,391,192 A | 2/1995 | Lu et al. | 607/28 |
| 5,425,373 A | 6/1995 | Causey, III | 128/697 |
| 5,435,316 A | 7/1995 | Kruse | 128/697 |
| 5,437,285 A | 8/1995 | Verrier et al. | 128/702 |
| 5,448,997 A | 9/1995 | Kruse et al. | 128/697 |
| 5,462,060 A | 10/1995 | Jacobson et al. | 128/702 |
| 5,476,485 A | 12/1995 | Weinberg et al. | 607/28 |
| 5,522,857 A * | 6/1996 | van Krieken | 607/9 |
| 5,527,347 A | 6/1996 | Shelton et al. | 607/9 |
| 5,555,888 A | 9/1996 | Brewer et al. | 128/702 |
| 5,560,370 A | 10/1996 | Verrier et al. | 128/705 |
| 5,564,430 A | 10/1996 | Jacobson et al. | 128/697 |
| 5,613,495 A | 3/1997 | Mills et al. | 128/696 |
| 5,620,472 A | 4/1997 | Rahbari | 607/27 |
| 5,626,621 A | 5/1997 | Skoglund et al. | 607/10 |
| 5,658,320 A | 8/1997 | Betzold et al. | 607/14 |
| 5,683,432 A | 11/1997 | Goedeke et al. | 607/32 |
| 5,694,943 A | 12/1997 | Brewer et al. | 128/702 |
| 5,702,425 A | 12/1997 | Wickham | 607/9 |
| 5,709,213 A | 1/1998 | Kruse et al. | 128/696 |
| 5,755,739 A | 5/1998 | Sun et al. | 607/14 |
| 5,766,227 A | 6/1998 | Nappholz et al. | 607/9 |
| 5,766,232 A | 6/1998 | Grevious et al. | 607/60 |
| 5,776,167 A | 7/1998 | Levine et al. | 607/9 |
| 5,782,876 A | 7/1998 | Flammang | 607/4 |
| 5,813,991 A | 9/1998 | Willis et al. | 600/510 |
| 5,817,135 A | 10/1998 | Cooper et al. | 607/17 |
| 5,836,989 A | 11/1998 | Shelton | 607/27 |
| 5,842,997 A | 12/1998 | Verrier et al. | 600/518 |
| 5,843,139 A | 12/1998 | Goedeke et al. | 607/32 |
| 5,861,013 A | 1/1999 | Peck et al. | 607/28 |
| 5,871,512 A | 2/1999 | Hemming et al. | 607/28 |
| 5,873,898 A | 2/1999 | Hemming et al. | 607/28 |
| 5,899,928 A | 5/1999 | Sholder et al. | 607/27 |
| 5,921,940 A | 7/1999 | Verrier et al. | 600/518 |
| 5,954,661 A | 9/1999 | Greenspon et al. | 600/510 |
| 5,954,666 A | 9/1999 | Snell | 600/523 |
| 5,954,756 A | 9/1999 | Hemming et al. | 607/28 |
| 6,067,472 A | 5/2000 | Vonk et al. | 607/28 |
| 6,112,119 A | 8/2000 | Schuelke et al. | 607/9 |
| 6,169,918 B1 * | 1/2001 | Haefner et al. | 607/9 |
| 6,304,778 B1 | 10/2001 | Gilkerson et al. | 607/5 |
| 6,321,115 B1 | 11/2001 | Mouchawar et al. | 607/9 |
| 6,381,494 B1 | 4/2002 | Gilkerson et al. | 607/27 |
| 6,505,071 B1 | 1/2003 | Zhu et al. | 607/28 |
| 6,687,539 B2 | 2/2004 | Gilkerson et al. | 607/5 |

* cited by examiner

IMPLANTABLE PULSE GENERATOR AND METHOD HAVING ADJUSTABLE SIGNAL BLANKING

TECHNICAL FIELD

The present invention concerns implantable medical devices, and more particularly concerns implantable pulse generators having adjustable signal blanking intervals.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias includes the use of an implantable pulse generator. An implantable pulse generator is implanted in the patient and delivers therapy to the patient's heart under certain predetermined conditions.

An implantable pulse generator can be, among other things, a pacemaker. A pacemaker delivers timed sequences of low energy electrical stimuli, called pace pulses, to the heart, such as via an intravascular lead (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. A pacemaker is often used to treat patients with bradyarrhythmias, that is, hearts that beat too slowly, or irregularly.

An implantable pulse generator can also be a cardioverter/defibrillator. A cardioverter/defibrillator is capable of delivering higher energy electrical stimuli to the heart. The cardioverter/defibrillator is often used to treat a patient with a tachyarrhythmia, that is, a heart that beat too quickly. Such too-fast heart rhythms also cause diminished blood circulation because the heart isn't allowed sufficient time to fill with blood before contracting to expel the blood. Such pumping by the heart is inefficient. A cardioverter/defibrillator is capable of delivering a high energy electrical stimulus that is sometimes referred to as a defibrillation countershock. The countershock interrupts the tachyarrhythmia, allowing the heart to reestablish a normal rhythm for the efficient pumping of blood. In addition to the pacemaker and the cardioverter/defibrillator, an implantable pulse generator can combine the function of the pacemaker and the cardioverter/defibrillator, drug delivery devices, and any other implantable or external systems or devices for diagnosing or treating cardiac arrhythmias.

A typical pacemaker and/or cardioverter/defibrillator include one or more electrical leads, which extend from a sealed housing of the pulse generator through the venous system into the inner walls of a heart. Within the housing are a battery for supplying power, a capacitor for delivering bursts of electric current through the leads to the heart, and monitoring circuitry for monitoring the heart and determining not only when and where to apply the current bursts but also their number and magnitude. The monitoring circuitry generally includes a microprocessor and a memory that stores instructions directing the microprocessor to interpret electrical signals that naturally occur in the heart as normal or abnormal rhythms. For abnormal rhythms, the instructions, or more generally signal-processing algorithm, tell the processor what, if any, electrical therapy should be given to restore normal heart function.

In general, these algorithms use the time intervals between successive heart beats, or cardiac events, as key determinants of therapy decisions. Thus, to ensure the validity of therapy decisions, it is very important to ensure accuracy of these intervals. Determining these intervals can be especially problematic in a dual-chamber pacemaker and/or cardioverter/defibrillator. In the dual chamber device, a cardiac signal is monitored from two chambers of the heart, such as the right ventricle and the right atrium. In this device, there is a significant risk of mistaking a ventricle beat for an atrial beat, and therefore counting too many atrial beats and miscalculating some atrial intervals (the time between atrial beats).

In addition to mistaking sensed signals from cardiac chambers, "noise" from non-cardiac sources can also be problematic for the pacemaker and/or cardioverter/defibrillator. Noise interferes with the proper operation of the device, and is most commonly caused by external electrical interference. The response of the implanted device in the presence of noise, or interference, is important in ensuring the device is ready to provide therapy to the patient regardless of the presence of noise.

Thus, there is a need in the art for effective ways of addressing noise sensed in cardiac signals sensed by an implanted pulse generator, and maintaining a proper response of the implantable pulse generator in the presence of such noise.

SUMMARY OF THE INVENTION

The present subject matter provides an implantable pulse generator and a method of its operation that fulfills the aforementioned needs, along with other needs in the art. The implantable pulse generator initiates a blanking window during sensed cardiac signals in response to certain predetermined conditions. These conditions include a sensed cardiac event and/or a paced cardiac event. The blanking window includes a repeatable portion that is triggered by noise sensed in the cardiac signal. When triggered, the repeatable portion of the blanking window extends blanking window, thus preventing noise from being included in the analysis of and response to the sensed cardiac signals.

In an exemplary embodiment, the implantable pulse generator includes a first cardiac lead having one or more electrodes, where the one or more electrodes are coupled to a signal sensor to sense a first cardiac signal. The pulse generator further includes a blanking window initiator coupled to the signal sensor. The blanking window initiator identifies cardiac events, sensed or paced, in the first cardiac signal and starts a blanking interval in response to an identified cardiac event. The blanking window is an interval of time during which a sensed cardiac signal is ignored by the implantable pulse generator.

The blanking interval further includes a repeatable noise window blanking interval. The repeatable noise window blanking interval is a portion of the blanking interval that is repeated if noise is detected in the sensed cardiac signal during the repeatable noise window. In one embodiment, noise includes sensed signals having a predetermined frequency range.

A noise detector is further coupled to the signal sensor and the blanking window initiator. In one embodiment, the noise detector analyzes the first cardiac signal to detect noise in the first signal. When noise is detected in the first signal during the repeatable noise window blanking interval portion of the blanking window, the blanking window initiator repeats the repeatable noise window blanking interval.

When the repeatable noise window blanking interval is being repeated, the noise detector sums a duration of repeated repeatable noise window blanking intervals. When the sum of the duration of the repeated noise window blanking becomes greater than a pacing escape interval, the noise detector issues a first signal to start delivery of asynchronous pacing pulses. When the noise signal ceases or is no longer detected, the noise detector issues a second signal to stop delivery of asynchronous pacing pulses.

In an alternative embodiment, the noise detector sums repeated noise window blanking intervals to give a duration of the repeatable noise window blanking intervals. This value is then compared to the pacing escape interval. When the duration of the repeatable noise window blanking intervals is greater than the pacing escape interval, the noise detector repeats the pace escape interval. Once the noise ceases, the noise detector issues a first signal to resume pacing after one pacing escape interval.

In an additional embodiment, the implantable pulse generator further includes a second cardiac lead having one or more electrodes that are used to sense a second cardiac signal. When two cardiac signals are sensed (e.g., the first cardiac signal and the second cardiac signal), which cardiac signal is blanked (i.e., sensed but the signal is ignored by the implantable pulse generator) depends upon where the cardiac signals are being sensed from the heart and what type of cardiac complex is being sensed. For example, when the first cardiac signal is an atrial signal and the second cardiac signal is a ventricular signal, a sensed atrial contraction in the atrial signal initiates the blanking interval in the ventricular signal. Similarly, when the first cardiac signal is the ventricular signal and the second cardiac signal is the atrial signal, a sensed ventricular contraction in the ventricular signal initiates the blanking interval in the atrial signal.

In a further embodiment, the duration of the blanking interval also depends upon the type of cardiac event sensed in the cardiac signal. For example, the blanking window initiator identifies cardiac events as either sensed intrinsic cardiac events or paced cardiac events. Based on the identification of the sensed cardiac complex, the blanking window initiator adjusts the blanking interval to a first overall duration when a paced cardiac event is identified and to a second overall duration when a sensed cardiac event is identified.

These and other embodiments, aspects, advantages, and features will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
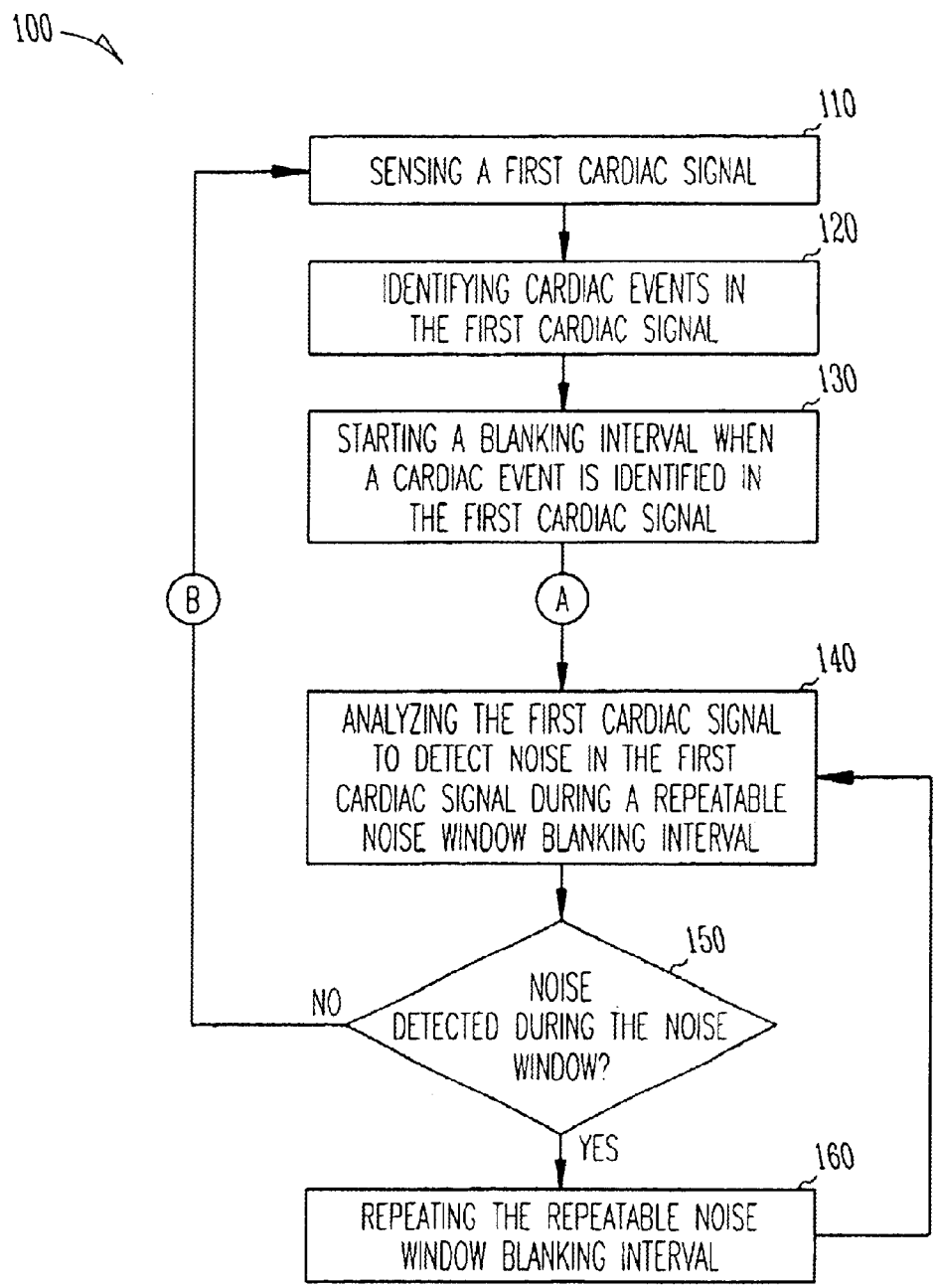
FIG. 1 shows a flow chart illustrating an exemplary method of the present subject matter.

FIG. 1 shows a flow chart 100, illustrating an exemplary method of the present subject matter. At 110, a first cardiac signal is sensed. In one embodiment, the first cardiac signal is sensed from any number of locations on or within the heart. For example, the first cardiac signal is sensed from a right ventricular location, or from a right atrium location. Alternatively, the first cardiac signal is sensed from a cardiac region that is adjacent to either the left atrium or the left ventricle. The cardiac signal can also be sensed from a cardiac region that is between these two regions of the heart. In an additional embodiment, the first cardiac signal is either a far field signal, also referred to as a morphology signal, or a near field signal, also referred to as a rate signal. Electrode structures and lead configurations with these electrodes are known.

At 120, as the first cardiac signal is sensed, cardiac events are detected and identified in the first cardiac signal. In one embodiment, the cardiac events are identified by analyzing the cardiac signal for complexes that exceed a dynamic threshold value, as is known. When a cardiac event is detected, a blanking interval is started at 130. In one embodiment, the blanking interval is a time interval during which sensing of the cardiac signal is suspended, and therefore, the information contained in the cardiac signal during this interval is ignored. Blanking intervals are applied in implantable pulse generators having electrodes implanted in only a single chamber. Alternatively, when the blanking interval is used with a dual-chamber pulse generator (e.g., electrodes in two or more chambers of the heart), the blanking interval is intended to prevent the inappropriate detection of signals from an opposite chamber, commonly referred to as crosstalk.

The blanking interval started when the cardiac event is identified in the first cardiac signal at 130 further includes a repeatable noise window blanking interval. The repeatable noise window blanking interval is a portion of the blanking interval that is repeatable or retriggerable when noise is detected in the sensed cardiac signal. During this interval, the first cardiac signal is sensed or monitored for the presence of noise, or interference. At 140 the first cardiac signal is analyzed to detect noise in the first cardiac signal during the repeatable noise window blanking interval. At 150, when noise is not detected in the first cardiac signal during the repeatable noise window blanking interval, the blanking interval ends after expiring and returns to 110. The blanking interval is then begun again when the next cardiac event is detected.

When noise is detected during the repeatable noise window blanking interval at 150, the repeatable noise window blanking interval is repeated at 160. In one embodiment, the noise window blanking interval is immediately repeated once the noise is detected. Upon repeating the noise window blanking interval, the system returns to 140 to analyze the first cardiac signal for noise during the repeated noise window blanking interval, and proceeds through 150 and 160, if necessary, as previously described.

Figure 2:
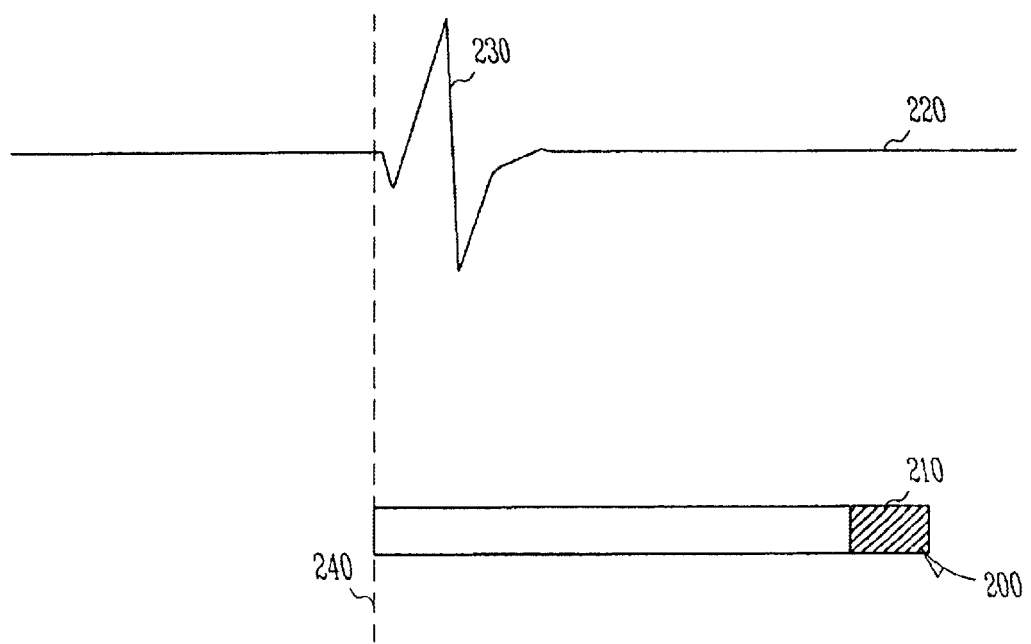
FIG. 2 is schematic of a blanking interval according to an exemplary embodiment of the present subject matter.

FIG. 2 is an exemplary embodiment showing the blanking interval 200. The blanking interval is shown with an absolute blanking period (during which all signals, regardless of origin, are ignored) followed by the repeatable noise window blanking interval 210, during which the first cardiac signal is monitored for noise signals having predetermined characteristics. In one embodiment, noise is identified as a signal having a predetermined frequency range, where the predetermined frequency range is a programmable value of greater than 50 Hz.

In addition, a cardiac signal 220 having a cardiac event 230 is shown in relation with the blanking interval 200. When the cardiac event 230 is detected the blanking interval 200 is started, as shown by the dashed line 240. During the duration of the blanking interval 200, sensing of the cardiac signal 220 is suspended, except for during the repeatable noise window blanking interval 210.

In one embodiment, the duration of the blanking period is either a programmable value or a set value. Which blanking period duration is used depends upon what type of initiator was used to produce the cardiac complex sensed in the first cardiac signal. For example, when the cardiac complex detected in the first cardiac signal is a paced cardiac complex (i.e., a pacing pulse is used to cause the heart to contract) the duration of the blanking interval is a programmable value in the range of 150 to 500 milliseconds. Alternatively, when the cardiac complex detected in the first cardiac signal is an intrinsic cardiac pulse (i.e., contraction started by the heart) the duration of the blanking interval is a set value of 135 milliseconds. The repeatable noise window blanking is a constant interval set at 40 milliseconds.

Figure 3:
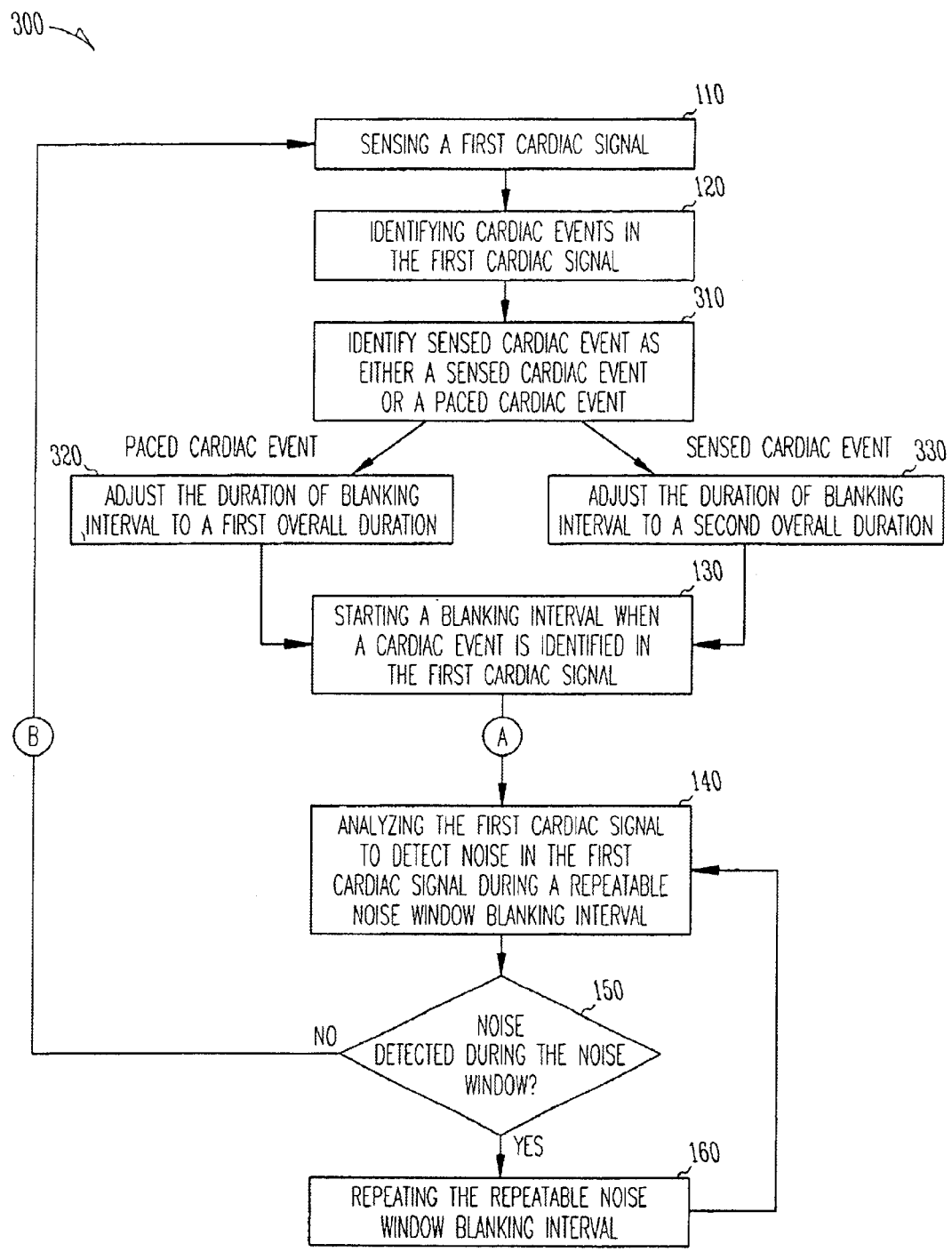
FIG. 3 shows a flow chart illustrating an exemplary method of the present subject matter.

FIG. 3 shows a flow chart 300, illustrating an exemplary method selecting the duration of the blanking period based on the nature of the sensed cardiac complex. The flow chart of FIG. 3 includes blocks described for FIG. 1 that will be briefly described. At 110, the first cardiac signal is sensed and cardiac events are detected and identified in the first cardiac signal at 120, as previously described. At 310, the sensed cardiac event are further identified as either a sensed cardiac event or a paced cardiac event. In one embodiment, a paced cardiac event is identified by the system delivering the pacing pulse, as the paced cardiac event occurs after the pacing pulse is delivered. When the paced cardiac event is identified, the duration of the blanking interval is adjusted to a first overall duration at 320. In one embodiment, the first overall duration is programmable value in the range of 150 to 500 milliseconds, as previously described. At 330, when the sensed cardiac event is identified as an intrinsic cardiac event, the duration of the blanking interval is adjusted to a second overall duration. In one embodiment, the second overall duration is a preset value of 135 milliseconds, as previously described.

As previously described, the blanking interval further includes the repeatable noise window blanking interval. The repeatable noise window blanking interval is positioned at a variety of locations along the blanking interval. The location of the noise window blanking interval depends upon which type of cardiac event is detected. For example, for a paced event the repeatable noise window blanking interval ends concurrently with the first overall duration of the blanking interval.

Alternatively, for a sensed intrinsic cardiac event the repeatable noise window blanking interval is adjustably programmed to start at any number of locations during the second overall duration of the blanking interval. In this embodiment, the second overall duration includes a first timed interval. The first timed interval is a programmable value and is an absolute blanking interval. The repeatable noise window blanking interval is then started after the first timed interval of the second overall duration. The repeatable noise window blanking interval then runs until it expires, where it is possible that a second timed interval could occur after the repeatable noise window blanking interval expires.

Figure 4A:
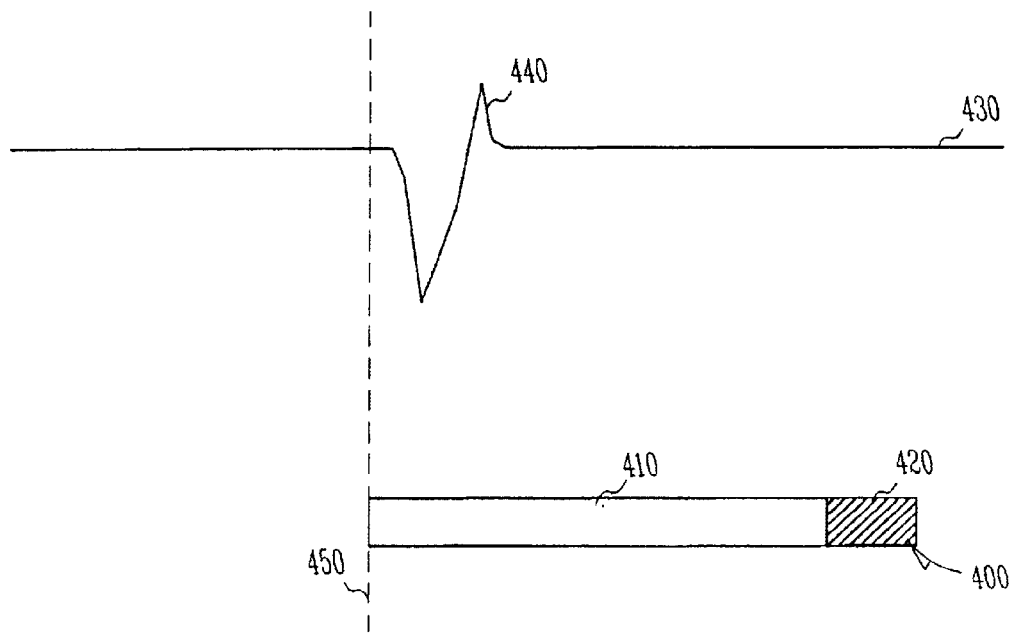
FIGS. 4A and 4B are schematics of a blanking interval according to exemplary embodiments of the present subject matter.
Figure 4B:
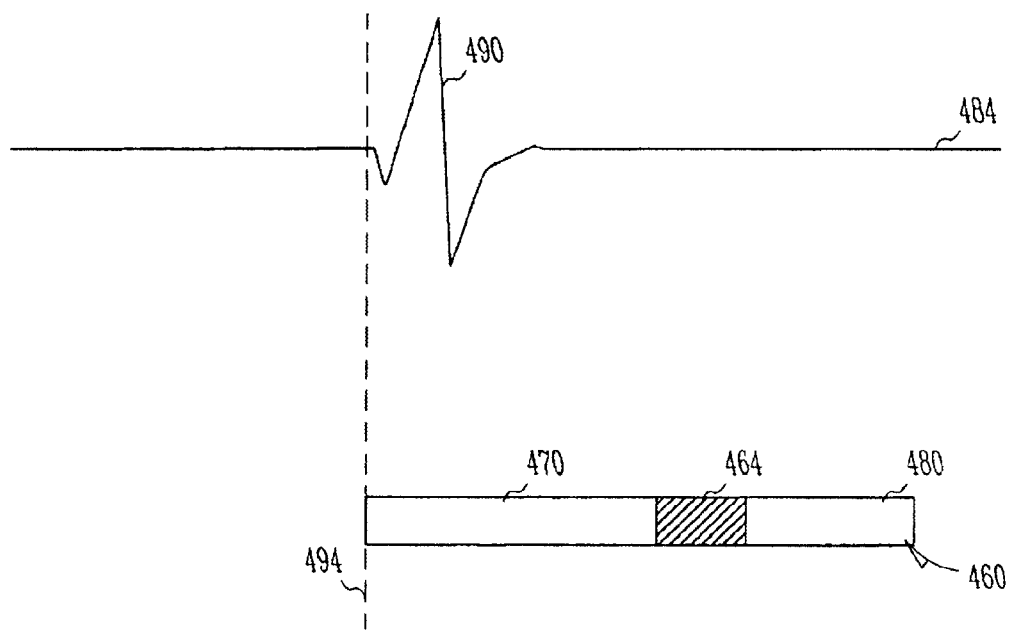

FIGS. 4A and 4B show exemplary embodiments of adjusting the duration of the blanking period and the position of the repeatable noise window blanking interval based on the nature of the sensed cardiac complex. In FIG. 4A, there is shown a blanking interval 400 having an absolute blanking interval 410. The absolute blanking interval 410 is followed by the repeatable noise window blanking interval 420. FIG. 4A also shows a cardiac signal 430 with a paced cardiac event 440 is shown in relation with the blanking interval 400. When the paced cardiac event 440 is detected, the blanking interval 400 is started, as shown by the dashed line 450. During the duration of the blanking interval 400, sensing of the cardiac signal 430 is suspended, except for during the repeatable noise window blanking interval 420. As previously discussed, the duration of the blanking interval 400, which includes the repeatable noise window blanking interval 420, is a programmable value. The repeatable noise window blanking interval 420 also expires at the same time the blanking interval 400 expires, provided noise is not sensed during the repeatable noise window blanking interval 420. The repeatable noise window blanking interval is 40 milliseconds, as previously described.

In FIG. 4B, there is shown a blanking interval 460 that includes a repeatable noise window blanking interval 464. In contrast to FIG. 4A, the position of the repeatable noise window blanking interval 464 along the blanking interval 460 is adjustably programmed to start at any number of locations during the second overall duration of the blanking interval 420. The second overall duration of the blanking interval 460 includes a first timed interval 470 that is a programmable value in the range of 5 to 45 milliseconds.

The first timed interval is an absolute blanking interval and is followed by the repeatable noise window blanking interval 464. After the repeatable noise window blanking interval 464 expires, a second timed interval 480 begins. In one embodiment, the second timed interval 480 is an absolute refractory period. The duration of the second timed interval 480 is determined when the first timed interval 470 is set, as the duration of the repeatable noise window blanking interval 464 is a set value at 40 milliseconds. FIG. 4B also shows a cardiac signal 484 with a sensed cardiac event 490 is shown in relation with the blanking interval 460. When the sensed cardiac event 490 is detected, the blanking interval 460 is started, as shown by the dashed line 494. During the duration of the blanking interval 460, sensing of the cardiac signal 484 is suspended, except for during the repeatable noise window blanking interval 464.

Figure 5:
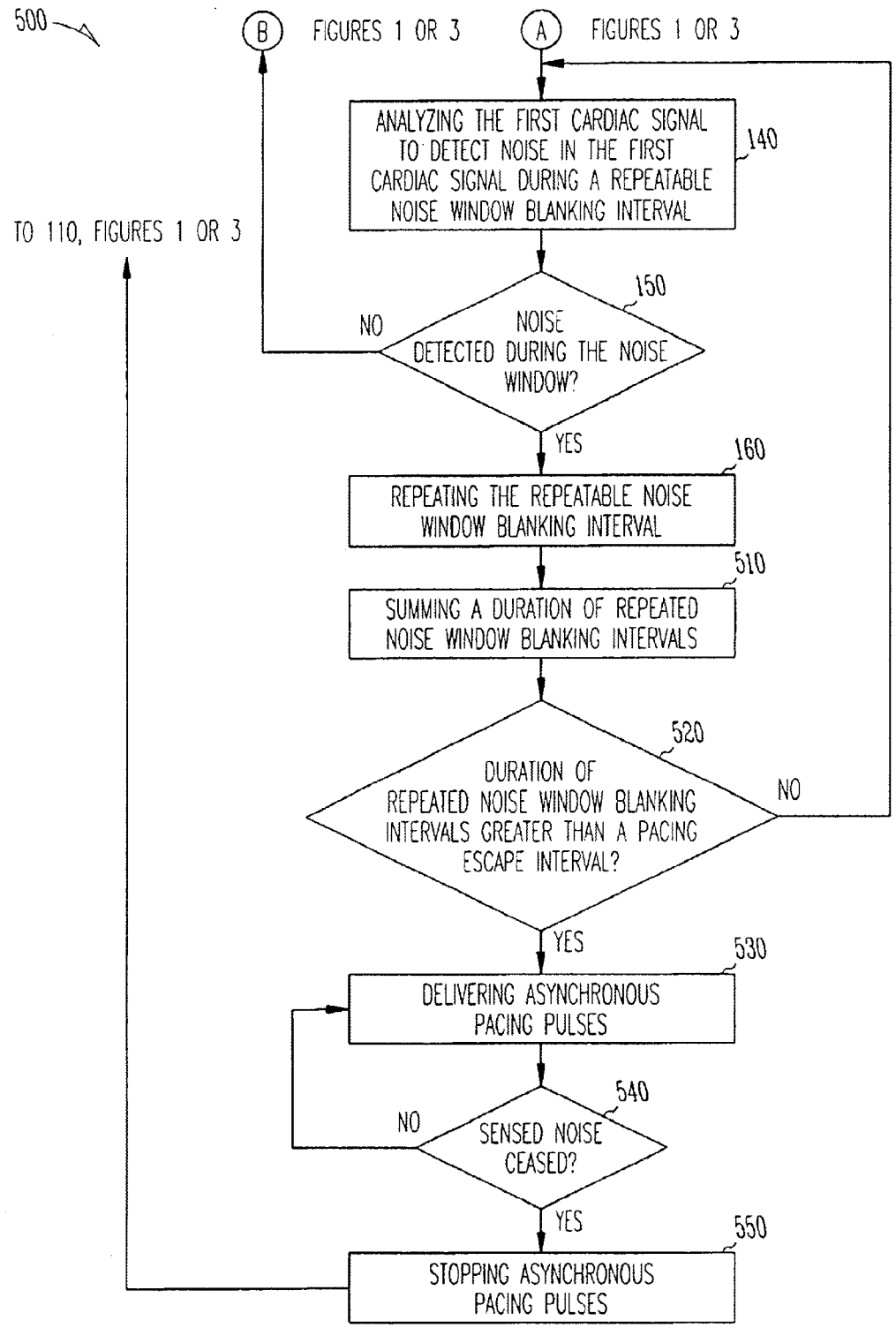
FIG. 5 shows a flow chart illustrating an exemplary method of the present subject matter.

FIG. 5 shows a flow chart 500, illustrating an exemplary method of the present subject matter, where the encircled A and the encircled B connect to the corresponding encircled A and encircled B in either FIG. 1 or FIG. 3. Blocks 140, 150 and 160 are as previously described, except the method does not return to 140 after 160. After 160, the system proceeds to 510, where the sum of the repeated noise window blanking intervals is determined. At 520, the sum of the repeated noise window blanking intervals is then compared to a pacing escape interval to determine if the sum is greater than a pacing escape interval. In one embodiment, the pacing escape interval is the period between the detected cardiac event (sensed or paced) and the next cardiac event (sensed or paced). In one embodiment, the duration of the pacing escape interval is a programmable value in the range of 2000 to 342 milliseconds.

At 530, when the sum of the repeated noise window intervals is greater than the pacing escape interval, asynchronous pacing pulses are delivered to the heart. At 540, the system determines when the sensed noise has ceased. When the noise has not ceased, the system returns to 530. Alternatively, when the noise does cease, the system proceeds to 550, where the asynchronous pacing pulses are then stopped. The system then returns to sensing the first cardiac signal at 110.

Figure 6:
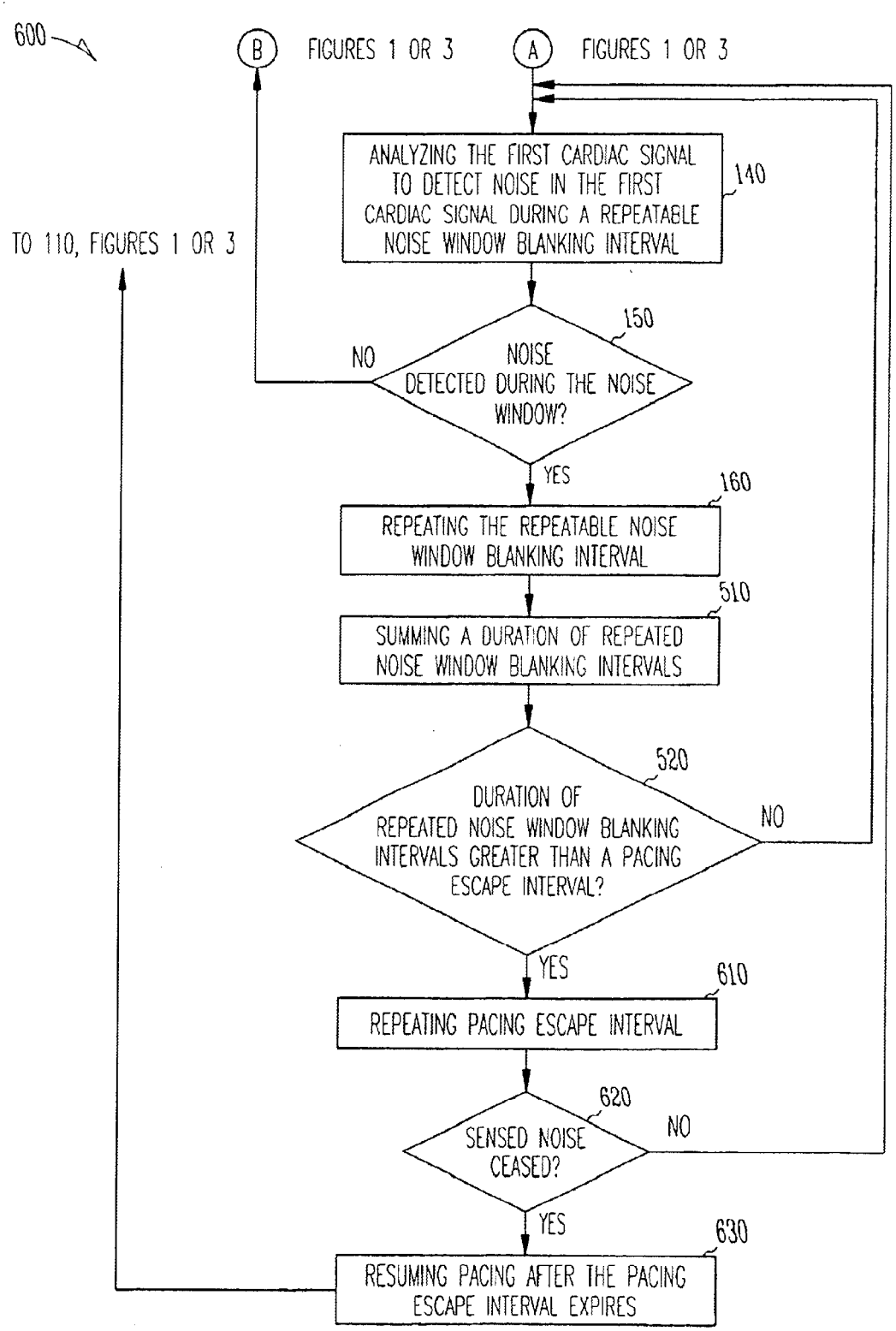
FIG. 6 shows a flow chart illustrating an exemplary method of the present subject matter.

FIG. 6 shows a flow chart 600, illustrating an additional exemplary method of the present subject matter, where the encircled A and the encircled B connect to the corresponding encircled A and encircled B in either FIG. 1 or FIG. 3. Blocks 140, 150 and 160 are as previously described, except the method does not return to 140 after 160. After 160, the system proceeds to 510, where the sum of the repeated noise window blanking intervals is determined. At 520, the sum of the repeated noise window blanking intervals is then compared to a pacing escape interval to determine if the sum is greater than a pacing escape interval, as previously described. At 610, when the sum of the repeated noise window intervals is greater than the pacing escape interval, the pacing escape interval is repeated. At 620, the system determines when the sensed noise has ceased. If the noise has not ceased, the system returns to 140. If the noise has ceased, the system proceeds to 630 where the pacing is resumed after the pacing escape interval expires. The system then returns to sensing the first cardiac signal at 110.

Figure 7:
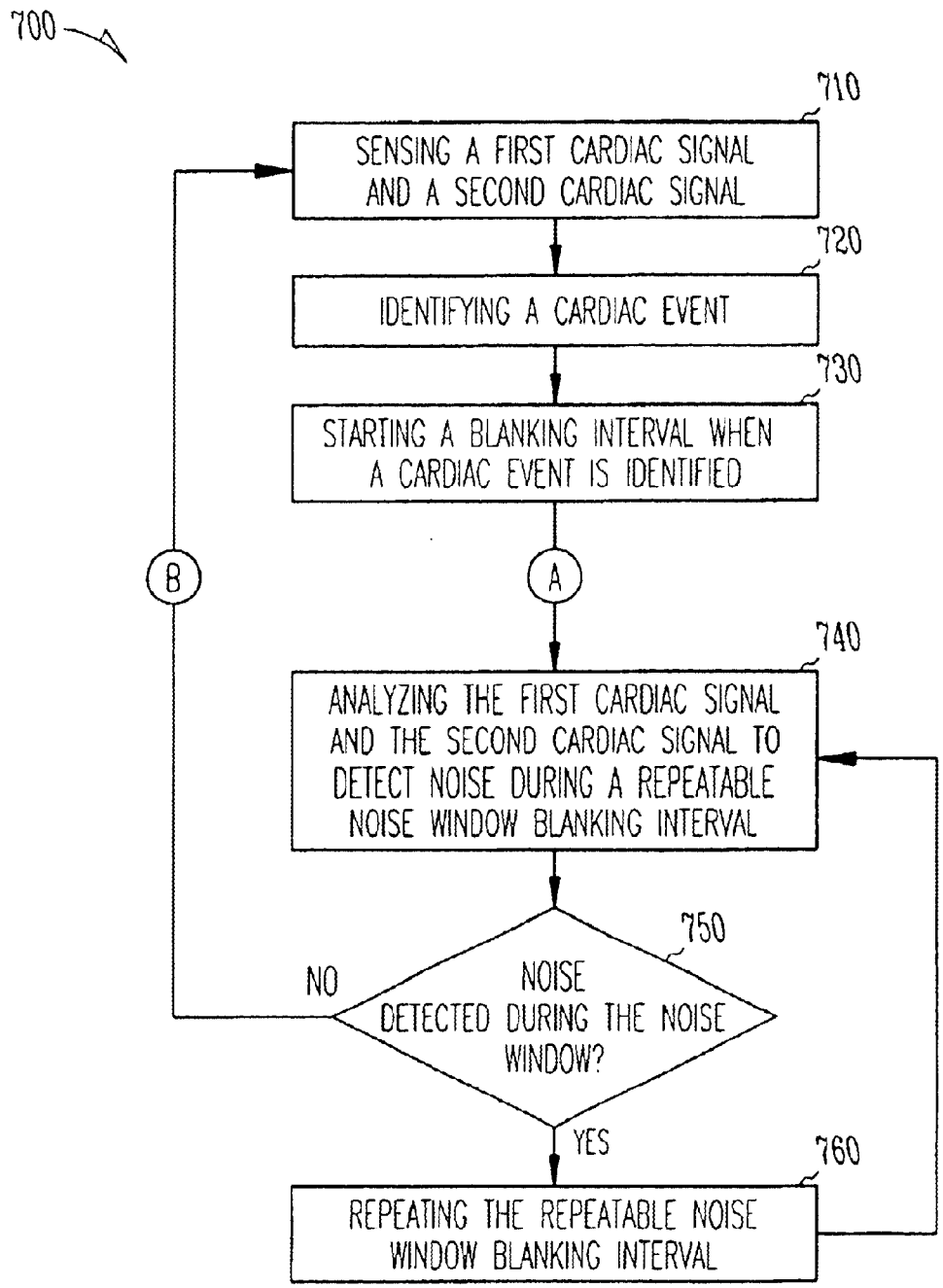
FIG. 7 shows a flow chart illustrating an exemplary method of the present subject matter.

FIG. 7 shows a flow chart 700, illustrating an additional exemplary method of the present subject matter. At 710, a first cardiac signal and a second cardiac signal are sensed. In one embodiment, the first cardiac signal and the second cardiac signal are sensed from different cardiac regions. For example, the first cardiac signal is a ventricular signal sensed from a right ventricular location or a location adjacent a left ventricular location and the second cardiac signal is an atrial signal sensed from a right atrium location or a location adjacent a left atrium. Alternatively, the first cardiac signal is an atrial signal sensed from a right atrium location or a location adjacent a left atrium location and the second cardiac signal is a ventricular signal sensed from a right ventricle location or a location adjacent a left ventricle. The first and second cardiac signals are each either a near field signal or a far field signal, as previously described.

At 720, as the first cardiac signal is sensed, cardiac events are detected and identified in the first cardiac signal. When the cardiac event is detected in the first cardiac signal, a blanking interval is started at 730 in the first and second cardiac signals so as to prevent the inappropriate detection of signals from an opposite chamber. In one embodiment, the atrial signal is sensed for the first cardiac signal and the ventricular signal is sensed for the second cardiac signal, where an atrial contraction in the atrial signal is identified as the cardiac event and both the ventricular signal and atrial signal are blanked during the blanking interval. In an alternative embodiment, the ventricular signal is sensed for the first cardiac signal and the atrial signal is sensed for the second cardiac signal, where a ventricular contraction in the ventricular signal is identified as the cardiac event and both the ventricular signal and atrial signal are blanked during the blanking interval.

At 740 both the first cardiac signal and the second cardiac signal are analyzed to detect noise during the repeatable noise window blanking interval. At 750, when noise is not detected in the cardiac signals during the repeatable noise window blanking interval, the blanking interval ends after expiring and returns to 710. The blanking interval is then begun again when the next cardiac event is detected. When noise is detected during the repeatable noise window blanking interval at 750, the repeatable noise window blanking interval is repeated at 760. Upon repeating the noise window blanking interval, the system returns to 740 to analyze the cardiac signals for noise during the repeated noise window blanking interval, and proceeds through 750 and 760, if necessary, as previously described. The subject matter described for FIGS. 3, 5 and 6 can also be extended to include an analysis and utilization of both the first and the second cardiac signal.

Figure 8:
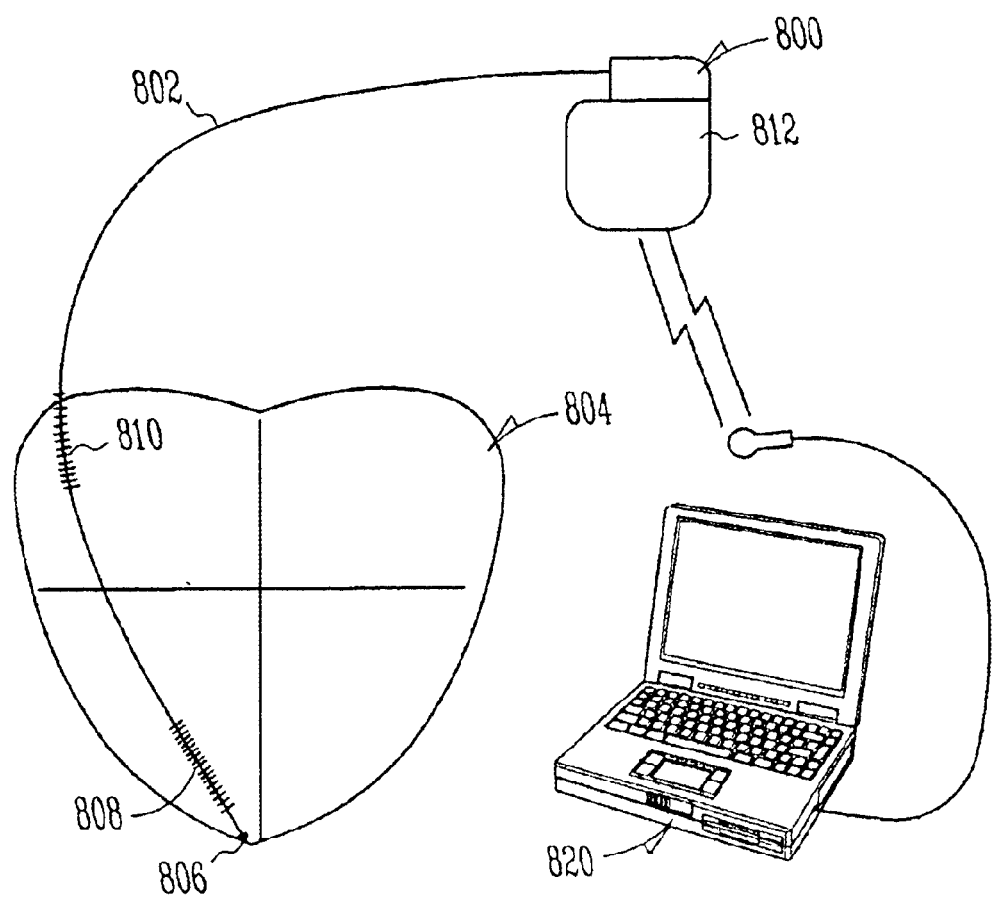
FIG. 8 shows a perspective view of an exemplary embodiment of an implantable pulse generator partially implanted in a heart from which segments have been removed to show detail.

FIG. 8 shows an exemplary embodiment of a pulse generator 800. The pulse generator 800 includes a first cardiac lead 802 having one or more electrodes. In one embodiment, the first cardiac lead 802 is a ventricular lead adapted to be implanted within a heart 804. The first cardiac lead 802 includes at least a sense/pace electrode 806, a first defibrillation electrode 808 and a second defibrillation electrode 810. FIG. 8 shows an embodiment in which the sense/pace electrode 806 is a tip electrode located at the distal end of lead 802 and the first and second defibrillation electrodes are coil electrodes.

The first cardiac lead 802 is releasably coupled to the implantable pulse generator 800 so as to couple electrodes 806, 808 and 810 to the electronic circuitry within the pulse generator 800. This allows for cardiac signals to be sense from and electrical energy pulses to be delivered to the heart 804. In one embodiment, a first cardiac signal, as previously described, is sensed between the sense/pace electrode 806 and the first defibrillation electrode 808. Additionally, a second cardiac signal, as previously described can be sensed between either the first defibrillation electrode 808 and the second defibrillation electrode 810 or between the a second defibrillation electrode 810 and the housing 812 of the implantable pulse generator 800. A medical device programmer 820 is also shown in FIG. 8, where the medical device programmer 820 and the electronic circuitry within the implantable pulse generator 800 are adapted to establish a communication link so as to allow for transfer of data and instructions to and from the devices. In one embodiment, communication between the medical device programmer 820 and the implantable pulse generator 800 is established over a radio frequency telemetry channel as is known in the art.

Figure 9:
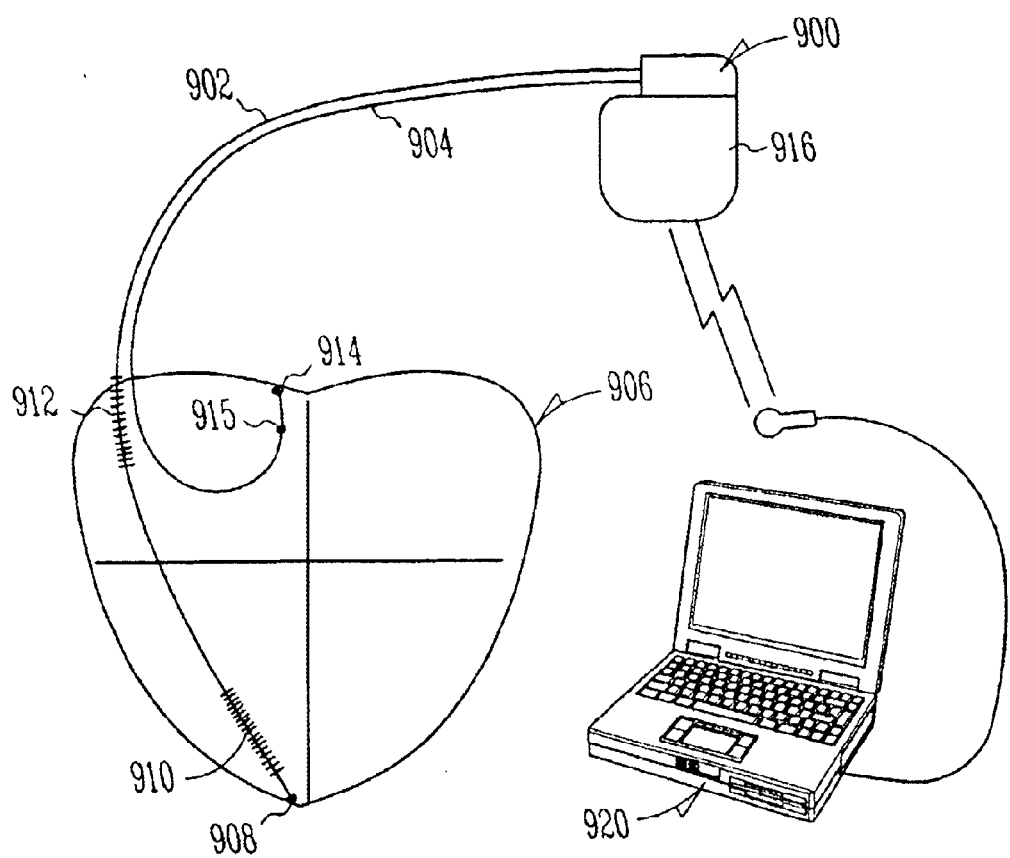
FIG. 9 shows a perspective view of an exemplary embodiment of an implantable pulse generator partially implanted in a heart from which segments have been removed to show detail.

FIG. 9 shows an additional exemplary embodiment of a pulse generator 900. The implantable pulse generator 900 includes a first cardiac lead 902 having one or more electrodes and a second cardiac lead 904 having one or more electrodes. In one embodiment, the first cardiac lead 902 is a ventricular lead adapted to be implanted within a heart 906. The first cardiac lead 902 includes at least a sense/pace electrode 908, a first defibrillation electrode 910 and a second defibrillation electrode 912. FIG. 9 shows an embodiment in which the sense/pace electrode 908 is a tip electrode located at the distal end of lead 902 and the first and second defibrillation electrodes are coil electrodes. The second cardiac lead 904 includes a first electrode 914 and a second electrode 915, where the first electrode 914 is shown positioned at the distal end of the second lead 904 and the second electrode 915 is shown positioned proximal the first electrode 914 along the second cardiac lead 904.

The first cardiac lead 902 and the second cardiac lead 904 are releasably coupled to the implantable pulse generator 900 so as to couple electrodes 908, 910, 912, 914 and 914 to the electronic circuitry within the pulse generator 900. This allows for cardiac signals to be sensed from and for electrical energy pulses to be delivered to the heart 906. In the present embodiment, a first cardiac signal is sensed between the first electrode 914 and the second electrode 915. Alternatively, the first cardiac signal is sensed between either the first and/or second electrode 914, 915 and an electrically conductive portion of the implantable cardiac defibrillator housing 916. A second cardiac signal is sensed between the sense/pace electrode 908 and the first defibrillation electrode 910. Additionally, a second cardiac signal can be sensed between either the first defibrillation electrode 910 and the second defibrillation electrode 912. A medical device programmer 920 is also shown in FIG. 9, where the medical device programmer 920 and the electronic circuitry within the implantable pulse generator 900 are adapted to establish a communication link so as to allow for transfer of data and instructions to and from the devices. In one embodiment, communication between the medical device programmer 920 and the implantable pulse generator 900 is established over a radio frequency telemetry channel as is known in the art.

Figure 10:
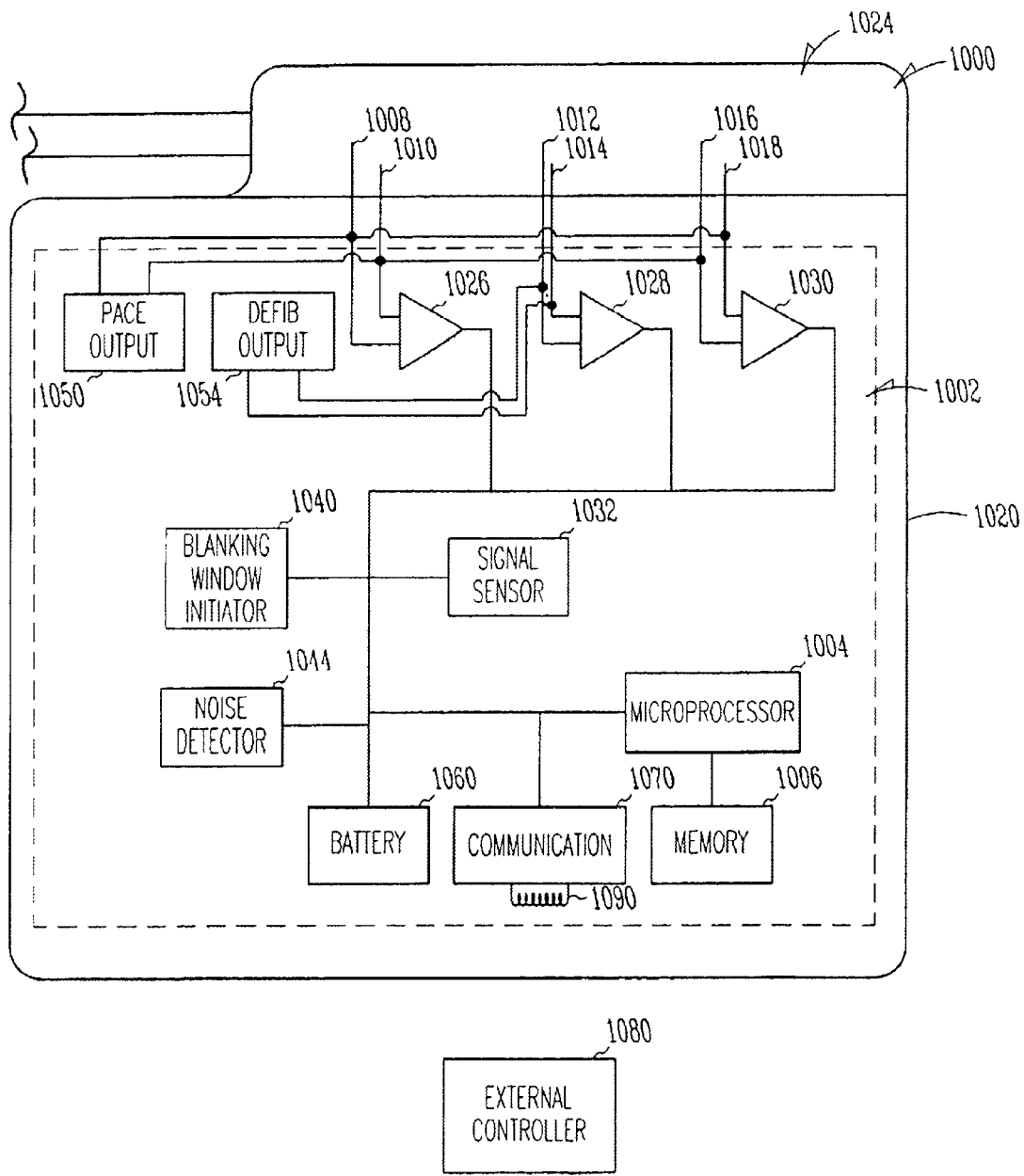
FIG. 10 shows an exemplary embodiment of a block diagram of an implantable pulse generator.

FIG. 10 shows an exemplary embodiment of a block diagram of an implantable pulse generator 1000. The implantable pulse generator 1000 includes control circuitry 1002 which receives one or more cardiac signals and delivers electrical energy to electrodes positioned on the atrial and/or ventricular leads under predetermined conditions. In one embodiment, the control circuitry 1002 is a programmable microprocessor-based system, with a microprocessor 1004 and a memory circuit 1006, which contains parameters for various pacing and sensing modes and stores data indicative of cardiac signals received by the control circuitry 1002. The control circuitry 1002 includes terminals labeled with reference numbers 1008, 1010, 1012, 1014 and 1016 for connection to the electrodes attached to the surface of a first and second lead. In the embodiment shown in FIG. 9, the sense/pace electrode 908 is coupled to terminal 1008 through a first electrically insulated conductor provided within the first lead 902. The first defibrillation electrode 910 is coupled to terminals 1010 and 1012 through a second electrically insulated conductor provided within the first lead 904. The second defibrillation electrode 912 is coupled to terminal 1014 through a third electrically insulated conductor provided within the first lead 904. Finally, the first electrode 914 and the second electrode 915 are coupled to terminals 1016 and 1018, respectively by electrically insulated conductors provided within the second lead 904.

The control circuitry 1002 is encased and hermetically sealed in a housing 1020 suitable for implanting in a human body. In one embodiment, the housing 1020 is made of titanium, however, other biocompatible housing materials as are known in the art may be used. A connector block 1024 is additionally attached to the housing 1020 to allow for the physical and the electrical attachment of the leads 902 and 904 and the electrodes to the implantable pulse generator 1000 and the encased control circuitry 1002.

Sense amplifiers 1026, 1028 and 1030 are coupled to the control circuitry 1002, and are electrically coupled to terminals 1008, 1010, 1012, 1014 1016 and 1018 to allow for at least a first cardiac signal and a second cardiac signal to be sensed, as previously described. The output of the sense amplifiers 1026, 1028 and 1030 are connected to a signal sensor 1032 to allow for the first and second cardiac signals to be sensed and analyzed according to the present subject matter. A blanking window initiator 1040 is coupled to the signal sensor, where the blanking window initiator 1040 identifies cardiac events in either the first cardiac signal or the second cardiac signal, as previously described. In one embodiment, the blanking window initiator 1040 starts the blanking interval when the cardiac event is identified in either the first cardiac signal or the second cardiac signal, as previously described.

A noise detector 1044 is coupled to the signal sensor 1032 and the blanking window initiator 1040, where the noise detector 1044 analyzes the first cardiac signal and the second cardiac signal to detect noise in either the first signal and/or the second signal during the repeatable noise window blanking interval, as previously described, where the blanking window initiator 1040 repeats the repeatable noise window blanking interval when the noise detector 1044 detects noise in either the first signal or the second signal during the noise window blanking interval.

In an additional embodiment, the blanking window initiator 1040 identifies sensed cardiac events and paced cardiac events. The blanking window initiator 1040 then adjusts the blanking interval to a first overall duration when a paced cardiac event is identified and to a second overall duration when a sensed cardiac event is identified, as previously discussed.

In a further embodiment, the noise detector 1044 sums the duration of repeated repeatable noise window blanking intervals. The noise detector 1044 then issues a first signal to start delivery of asynchronous pacing pulses when the duration of repeated repeatable noise window blanking intervals is greater than a pacing escape interval. Control circuitry 1002 includes a pace output 1050 and a defibrillation output 1054 for delivering pacing, cardioversion and/or defibrillation pulses through the electrodes, where the pace and defibrillation output 1050 and 1054 are both under the control of the microprocessor 1004. Power to the implantable pulse generator 1000 is supplied by an electrochemical battery 1060 that is housed within the pulse generator 1000. When the noise signal is no longer detected, the noise detector 1044 issues a second signal to stop delivery of asynchronous pacing pulses.

In an alternative embodiment, the noise detector 1044 sums repeated repeatable noise window blanking intervals to give a duration of the repeatable noise window blanking intervals. The noise detector 1044 compares the duration of the repeatable noise window blanking intervals to a pacing escape interval. The noise detector 1044 then repeats the pace escape interval when the duration of the repeatable noise window blanking intervals is greater than the pacing escape interval. When the noise signal is no longer detected, the noise detector 1044 issues a first signal to resume pacing after one pacing escape interval after the noise signal ceases, as previously discussed.

The blanking window initiator 1040 can blank one of both the first cardiac signal and/or the second cardiac signal, as previously discussed. In one embodiment, when the first cardiac signal is an atrial signal and the second cardiac signal is a ventricular signal, the blanking window initiator 1040 identifies the cardiac event as an atrial contraction in the atrial signal. Alternatively, when the first cardiac signal is a ventricular signal and the second cardiac signal is an atrial signal, the blanking window initiator 1040 identifies the cardiac event as a ventricular contraction in the ventricular signal.

Electronic communication circuitry 1070 is additionally coupled to the control circuitry 1002 to allow the pulse generator 1000 to communicate with an external controller 1080. In one embodiment, the electronic communication circuitry 1070 includes a data receiver and a data transmitter to send and receive and transmit signals and cardiac data to and from the external programmer 1080. In one embodiment, the data receiver and the data transmitter include a wire loop antenna 1090 to establish a radio frequency telemetric link, as is known in the art, to receive and transmit signals and data to and from the external controller 1080.

It is to be understood that the above description is intended to be illustrative, and not restrictive. Many other embodiments will be apparent to those of skill in the art upon reading and understanding the above description. For example, the present invention can be used with a variety of medical devices. Additionally, the Figures showing the exemplary embodiments herein are not to scale. Although the use of the lead has been described for use in a cardiac pacing system, the lead could also be applied to other types of body stimulating systems. The scope of the invention should, therefore, be determined with reference to the appended claims, along with the full scope of equivalents to which such claims are entitled.

We claim:

1. An implantable pulse generator, comprising:
   a first lead having one or more electrodes;
   a signal sensor coupled to one or more electrodes on the first cardiac lead to sense a first cardiac signal related to a heart;
   a blanking window initiator coupled to the signal sensor, wherein the blanking window initiator identifies cardiac events in the first cardiac signal, and wherein the blanking interval includes a repeatable noise window blanking interval; and
   a noise detector coupled to the signal sensor and the blanking window initiator, wherein the noise detector analyzes the first cardiac signal to detect noise identified by a predetermined noise frequency range in the first cardiac signal during the repeatable noise window blanking interval, wherein the blanking window initiator repeats the repeatable noise window blanking interval when the noise detector detects noise in the first cardiac signal during the repeatable noise window blanking interval; and
   wherein the blanking window initiator identifies sensed cardiac events and paced cardiac events, and wherein the blanking window initiator adjusts the blanking interval to a first overall duration when a paces cardiac event is identified and to a second different overall duration when a sensed cardiac event is identified.

2. The implantable pulse generator of claim 1, further comprising pace output circuit to deliver pacing pulses to the heart.

3. The implantable pulse generator of claim 2, wherein the first overall duration is a predetermined value in the range of 150 to 500 milliseconds.

4. The implantable pulse generator of claim 2, wherein the second overall duration is 135 milliseconds.

5. The implantable pulse generator of claim 2, wherein the repeatable noise window blanking interval runs and ends concurrently with the first overall duration of the blanking interval.

6. The implantable pulse generator of claim 2, wherein the second overall duration includes a first timed interval, and wherein the repeatable noise window blanking interval starts after the first timed interval of the second overall duration.

7. The implantable pulse generator of claim 6, wherein the first timed interval is a predetermined value in the range of 5 to 45 milliseconds.

8. The implantable pulse generator of claim 1, wherein the repeatable noise window blanking interval is 40 milliseconds.

9. The implantable pulse generator of claim 1, wherein the predetermined noise frequency range includes frequencies greater than 50 Hz.

10. The implantable pulse generator of claim 1, wherein the blanking window initiator blanks the first cardiac signal during the blanking interval.

11. The implantable pulse generator of claim 1, including a second cardiac lead having one or more electrodes coupled to the signal sensor to sense a second cardiac signal, wherein the blanking window initiator blanks the second cardiac signal during the blanking interval.

12. The implantable pulse generator of claim 11, wherein the first cardiac signal is an atrial signal, the second cardiac signal is a ventricular signal and the cardiac event is an atrial contraction identified by the blanking window initiator in the atrial signal.

13. The implantable pulse generator of claim 11, wherein the first cardiac signal is a ventricular signal, the second cardiac signal is an atrial signal and the cardiac event is a ventricular contraction identified by the blanking window initiator in the ventricular signal.

14. The implantable pulse generator of claim 1, further comprising a pace output circuit capable of delivering pacing pulses separated by a pacing escape interval to the heart, and wherein the noise detector sums a duration of repeated repeatable noise window blanking intervals, and issues a first signal to start delivery of asynchronous pacing pulses when the duration of repeated repeatable noise window blanking intervals is greater than the pacing escape interval.

15. The implantable pulse generator of claim 14, wherein the noise detector issues a second signal to stop delivery of asynchronous pacing pulses when the noise signal ceases.

16. The implantable pulse generator of claim 1, further comprising a pace output circuit capable of delivering pacing pulses separated a pacing escape interval to the heart, and wherein the noise detector sums repeated repeatable noise window blanking intervals to give a duration of the repeatable noise window blanking intervals, compares the duration of the repeatable noise window blanking intervals to the pacing escape interval, and wherein the noise detector repeats the pace escape interval when the duration of the repeatable noise window blanking intervals is greater than the pacing escape interval and issues a first signal to resume pacing pulse delivery after one pacing escape interval after the noise signal ceases.

17. A method, comprising:

sensing a first cardiac signal related to a heart;

identifying cardiac events in the first cardiac signal, including identifying a nature of each of the cardiac events;

adjusting a duration of a blanking interval based on the nature of the each of the cardiac events when the each of the cardiac events is identified in the first cardiac signal, wherein the blanking interval includes a repeatable noise window blanking interval;

starting the blanking interval;

detecting noise in the first cardiac signal during the repeatable noise window blanking interval; and repeating the repeatable noise window blanking interval.

18. The method of claim 17, including:

pacing the heart, and wherein:
    identifying cardiac events in the first cardiac signal includes identifying intrinsic cardiac events and paced cardiac events; and
    adjusting the duration of the blanking interval includes:
        adjusting the blanking interval to a first overall duration when each of the paced cardiac events is identified; and
        adjusting the blanking interval to a second overall duration when each of the intrinsic cardiac events is identified.

19. The method of claim 18, including programming the first overall duration in the range of 150 to 500 milliseconds.

20. The method of claim 18, including setting the second overall duration to 135 milliseconds.

21. The method of claim 18, including ending the repeatable noise window blanking interval concurrently with the first overall duration of the blanking interval.

22. The method of claim 18, wherein the second overall duration includes a first timed interval, and starting the repeatable noise window blanking interval after the first timed interval of the second overall duration.

23. The method of claim 22, including programming the first timed interval in the range of 5 to 45 milliseconds.

24. The method of claim 17, wherein detecting noise includes identifying noise as a signal having a predetermined frequency range.

25. The method of claim 17, including programming the predetermined frequency range of greater than 50 Hz.

26. The method of claim 17, including blanking the first cardiac signal during the blanking interval.

27. The method of claim 26, including sensing a second cardiac signal; and blanking the second cardiac signal during the blanking interval.

28. The method of claim 27, including sensing an atrial signal for the first cardiac signal; sensing a ventricular signal for the second cardiac signal; and identifying an atrial contraction in the atrial signal as the cardiac event.

29. The method of claim 27, including sensing a ventricular signal for the first cardiac signal; sensing an atrial signal for the second cardiac signal; and identifying a ventricular contraction in the ventricular signal as the cardiac event.

30. The method of claim 17, including summing a duration of repeated noise window blanking intervals; and delivering asynchronous pacing pulses when the duration of repeated noise window blanking intervals is greater than a pacing escape interval.

31. The method of claim 30, including stopping the asynchronous pacing pulses when the noise signal ceases.

32. The method of claim 17, including summing a duration of repeated noise window blanking intervals;

comparing the duration of repeated noise window blanking intervals to a pacing escape interval;

repeating the pace escape interval when the repeated noise window blanking intervals is greater than the pacing escape interval; and resume pacing after one pacing escape interval after the noise signal ceases.

33. The method of claim 17, including setting the repeatable noise window blanking interval to 40 milliseconds.

\* \* \* \* \*